United States Patent [19]

Chang et al.

[11] Patent Number: 5,679,662
[45] Date of Patent: Oct. 21, 1997

[54] SYNERGISTIC USE OF AZADIRACHTIN AND PYRETHRUM

[75] Inventors: Pauley Fei-Zan Chang, Ellicott City; James F. Walter, Ashton; Jerrold R. Harris, Columbia, all of Md.

[73] Assignee: Thermo Trilogy Corporation, Waltham, Mass.

[21] Appl. No.: 468,897

[22] Filed: Jun. 6, 1995

[51] Int. Cl.$^6$ .................. A01N 43/16; A01N 65/00
[52] U.S. Cl. ............ 514/66; 424/195.1; 514/65; 514/453; 514/72
[58] Field of Search ............... 514/65, 453, 66, 514/72; 424/195.1

[56] References Cited

U.S. PATENT DOCUMENTS

| | | | |
|---|---|---|---|
| 4,946,681 | 8/1990 | Walter | 424/195.1 |
| 5,001,146 | 3/1991 | Carter et al. | 514/453 |
| 5,124,349 | 6/1992 | Carter et al. | 514/453 |
| 5,281,618 | 1/1994 | Walter | 514/453 |
| 5,298,251 | 3/1994 | Locke et al. | 424/405 |
| 5,352,672 | 10/1994 | Staetz et al. | 514/65 |
| 5,356,628 | 10/1994 | Locke et al. | 424/405 |
| 5,368,856 | 11/1994 | Locke et al. | 424/195.1 |
| 5,372,817 | 12/1994 | Locke et al. | 424/405 |
| 5,397,571 | 3/1995 | Roland et al. | 424/405 |
| 5,405,612 | 4/1995 | Locke et al. | 424/410 |
| 5,409,708 | 4/1995 | Locke et al. | 424/410 |
| 5,411,736 | 5/1995 | Locke et al. | 424/410 |

FOREIGN PATENT DOCUMENTS 927892  6/1963  United Kingdom .

OTHER PUBLICATIONS

Lowery, D.T., et al., "Laboratory and Field Evaluation of Neem for the Control of Aphids (Homoptera: Aphididae)," *J. Econ. Entomol.*, 86:865–870 (1993).

Parmar, B.S., and S. Dutta, "Neem Oil as a Synergist for Insecticides," *Neem Newsletter*, 3:3–5 (1986).

Sharma, R.K., et al., "Aphidicidal Action of Neem (*Azadirachta indica* A. Juss) on Mustard Aphid, *Lipaphis erysimi* (Kalt.)," *Neem Newsletter*, 3:1–2 (1986).

*Primary Examiner*—Allen J. Robinson
*Attorney, Agent, or Firm*—Quarles & Brady

[57] ABSTRACT

In an insecticidal formulation containing Pyrethrum, addition of appropriate amounts of azadirachtin and clarified neem oil can significantly synergize the Pyrethrum activity while reducing or eliminating the need for Pipronyl butoxide as an agent to augment Pyrethrum activity. The disclosed formulations represent a significant cost advantage when compared to existing Pyrethrum/Pipronyl butoxide formulations.

6 Claims, No Drawings

SYNERGISTIC USE OF AZADIRACHTIN AND PYRETHRUM

FIELD OF THE INVENTION

The present invention relates to the field of naturally occurring insect toxic compounds, and more particularly to the combination of azadirachtin or clarified neem oil with Pyrethrum to increase the Pyrethrum activity.

BACKGROUND OF THE INVENTION

The neem tree, a tropical evergreen, is known to be the source of insect-toxic compounds that act as antifeedants, metamorphosis disrupters, chemosterilants and weak toxicants. Partially purified extracts from various portions of the neem tree retain insect-toxic activity. These extracts include clarified and crude neem oils, and neem waxes.

Azadirachtin, a hydrophilic, tetranorterpenoid, is the most thoroughly investigated insect-toxic compound that has been isolated from neem products. Azadirachtin comes in several closely related forms, the two most prominent of which are azadirachtin A and azadirachtin B. The azadirachtins are generally isolated from hexane extracts of neem and can be purified to a white microcrystalline powder by known methods. See, for example, Schroeder, D. R. and K. Nakanishi, *J. Natural Products* 50:241–4 (1987).

Because of their potent insect-toxic activity, neem extracts; and particularly the azadirachtins, have been targeted by entomologists as effective agents for biocontrol of insects. One line of investigation has been to determine whether any neem products show synergistic effectiveness in combination with other known insect-toxic products. In 1984, a synergistic interaction was observed between custard-apple (*Annona squamosa* L.) oil and neem oil against the rice green leaf hopper (*Nephotettix virenscens*) which interaction affected the transmission by the insect of the rice tungro virus. Mariappan, V. and R. C. Saxena, *J. Econ. Ent.*, 77:519–521 (1984). Pyrethrum is a botanical compound obtained from Pyrethrum plants found in Africa and South America. Although Pyrethrum, known since the early 1800s is recognized as safe, it is costly. Therefore, compositions that boost the specific activity of Pyrethrum are desired. Pyrethrum by itself is not very effective at concentrations below 0.02%. To increase Pyrethrum activity, Pipronyl butoxide (PBO) is typically added at about 0.16% or greater.

Efforts have also been made to synergize various neem seed extracts with Pipronyl Butoxide. Lange, W., "Natural Pesticides From the Neem Tree (*Azadirachta indica* A. Juss), "Proceedings of the Second International Neem Conference," pages 129–140, May 25–28, 1983. In 1986, Parmar and Dutta examined synergistic behavior of neem oil when placed in combination with various established insecticides. Parmar, B. S. and S. Dutta, "Neem Oil as a Synergist for Insecticides," *Neem News Letter*, 3:3–5 (1986). Parmar and Dutta tested neem seed oil extracted by seed pressing at various ratios of insecticide to synergist ranging from 1:1 to 1:5. Those authors reported that the neem seed oil tested significantly antagonized, rather than synergized, the activity of Pyrethrum, cutting the activity of Pyrethrum more than 50% when the two were mixed in equal amounts and eliminating all insecticidal activity of Pyrethrum at higher concentrations. In contrast, a synergistic effect was noted when neem oil was added to quinalphos and monocrotophos. Diamethoate was not affected by the presence of neem seed oil.

Pyrethrum is an insecticide that is primarily oxidatively metabolized in the insect system. Its antagonism by neem oil indicated to Parmar and Dutta that the oil could be acting as an oxidant or oxidation promoter to reduce the available concentration or level of Pyrethrum.

In a more recent study by Lowery, Isman and Brard (1993), the combination of Pyrethrum at 0.5% with either 0.002% azadirachtin or a solution of 0.002% azadirachtin with 1% expelled neem seed oil did not result in an increase in the activity of either the Pyrethrum or the neem products.

On the basis of these reports, one would be led to conclude that neither neem oil nor azadirachtin can synergize the activity of Pyrethrum.

SUMMARY OF THE INVENTION

The present invention is summarized in that conditions are described wherein the pest control activity of Pyrethrum can be increased synergistically when Pyrethrum is formulated either with azadirachtin, at a weight ratio of between 0.02 and 1 part per part of Pyrethrum, or with clarified neem oil, at a weight ratio of between 0.1 part and 100 parts per part of pyrethrum, or is formulated with both azadirachtin and clarified neem oil, in the above weight ratios.

The invention is further summarized in that the above formulations effectively control pests at absolute component concentrations significantly lower than have previously been disclosed. The ability to effectively control pests using a very dilute preparation results in significant cost saving over prior compositions.

The present invention is also summarized in that an effective pest control composition for application to a pest-infested surface comprises Pyrethrum at a concentration between 0.002% and 0.02% by weight, azadirachtin at a weight ratio of between 0.02 and 1 part per part of pyrethrum, and clarified neem oil, at a weight ratio of between 0.1 part and 100 parts per part of pyrethrum.

It is an object of the present invention to provide a formulation for effective pest control that uses less of the expensive pesticide pyrethrum than prior formulations, without sacrificing effectiveness.

It is a feature of the present invention that a formulation for effective pest control includes a synergistically effective amount of azadirachtin or clarified neem oil, or both.

It is a feature of the present invention that clarified neem oil or azadirachtin can substitute for pipronyl butoxide in the formulations of the present invention. Pipronyl butoxide at about 0.16% has previously been used to improve pyrethrum activity in formulations containing pyrethrum at less than 0.02%.

It is an advantage of the present invention that the formulation for effective pest control achieves control levels comparable to, or better than, existing pyrethrum-containing formulations, but uses significantly less pyrethrum in combination with one or more inexpensive synergistic agents.

Other objects, features and advantages of the present invention will become apparent upon consideration of the following detailed description.

DETAILED DESCRIPTION OF THE INVENTION

The pest control activity of Pyrethrum, with or without Pipronyl butoxide (PBO), is synergistically enhanced by combining it in a formulation with azadirachtin at a weight ratio of between 0.02 and 1 part per part of pyrethrum, or with clarified neem oil at a weight ratio of between 0.1 part and 100 parts per part of pyrethrum, or both azadirachtin and clarified neem oil in the above ratios.

The formulations demonstrate effective pest control activity even when diluted so that pyrethrum is present at between 0.002 and 0.02 percent by weight and the ratio of the other component or components are maintained.

Prior work has taught away from the use of formulations that include pyrethrum with azadirachtin or expelled neem oil. However, the present inventors here disclose that effective pest control, not seen in prior efforts, is achieved when azadirachtin or clarified neem oil, or both, are formulated in the indicated ratios. Control is achievable at very low input levels if the indicated ratio is maintained when the formulation is diluted for application as a pest control agent, and if the actual concentrations are sufficiently low.

The inventors attribute the activity of their formulation, and their ability to achieve activity where others have failed, to the use of clarified neem oil that lacks inhibitory factors present in crude neem oil such as expelled neem oil. Crude neem oil is not storage stable and can include as much as about 40% waxy substances.

The component concentrations reported herein in the examples are the actual concentrations applied in the examples by the inventors to insect infested surfaces. The tested formulations were prepared by diluting concentrated stock solutions to final dilutions over a range between 1:40 and 1:250. All stock solutions retained activity upon dilution to the tested concentration range, thus demonstrating that no negative concentration effects arise from providing the formulations as a concentrated stock for dilution before use. Thus, these formulations could be advantageously prepared in a concentrated form. However, it is noted that dilution to bring the component concentrations to an appropriate low level is preferred to achieve the synergistic pest control effect noted by the inventors.

In this application, a suitable measure of the pest control activity of the claimed formulations is an ability to kill adult or immature whiteflies. A typical commercially acceptable mortality level for a pesticide is in the range of 50% or higher mortality (at any life cycle stage) one week after a single application of the formulation. This test is suitable for evaluating the formulations disclosed and tested herein. Formulations having the disclosed component ratios can cause mortality of greater than 50%, and preferably greater than 60%, and most preferably greater than 75% of exposed pests.

Although killing of adult or immature whiteflies is a suitable test, pest control can be equivalently accomplished in ways other than those that result in death. For instance, an increased level of avoidance by insects of a plant or animal may constitute an effective level of control. Thus, even if mortality is not high, beneficial control can be realized. In this application, "pest control" is intended to encompass all forms of control including but not limited to insecticide, larvicide, nymphicide, and ovicide activities as well as avoidance activities. In non-insect targets, control can be attained at any stage of the life cycle. Particular compositions may be particularly effective on one or another stage of the life cycle. It is understood by the applicants that one of ordinary skill, in possession of this disclosure, is able to choose conditions suitable for pest control at any desired life cycle stage.

In this application, "clarified neem oil" (CNO) is intended to mean an oil extracted from neem seeds that is substantially free of azadirachtin and that has a cloud point of less than 13° C., as measured in ASTM D 2500-86 "Standard Test Method for Cloud-Point of Petroleum Oil." Clarified neem oil can be prepared from a neem oil extract. A neem oil extract can be obtained from neem seeds or from neem oil that has been physically expressed from the seeds by commonly practiced methods. However, clarification of expressed oil is less preferred than from oil prepared by solvent extraction from neem seeds. neem seeds are preferably coarsely ground before extraction of the neem oil.

Solvent extraction can be performed using a suitable non-polar, hydrophobic solvent. Suitable non-polar hydrophobic solvents for use in extracting neem oil from the neem seeds or expressed neem oil will include those non-polar hydrophobic solvents having high neem oil solubility and substantially no azadirachtin solubility. The preferred non-polar hydrophobic solvents include, but are not limited to, pentane, hexane, heptane, octane, nonane, decane, isooctane, cyclohexane, and isomers thereof; petroleum distillates, petroleum ether, and the like; aromatics such as benzene, toluene, and the like; substituted aromatics such as chlorobenzene, benzaldehyde, xylenes, and the like; and mixtures thereof. Various other non-polar-hydrophobic solvents having the above characteristics are well known to those skilled in the art, and the choice of a particular solvent is not critical, provided that the solvent is non-polar, hydrophobic, and exhibits little azadirachtin solubility and a high degree of neem oil solubility.

After solvent extraction, the solvent is then stripped from the neem oil extract at the lowest practical temperature to prevent degradation, preferably being removed by vacuum evaporation, although other methods may be used. The resulting clarified neem oil has a cloud point at or below 13° C.

The cloud point of crude neem oil can also be reduced to an acceptably low level by treating the crude oil with a dilute aqueous alkali solution (10%–30% by weight) at a temperature below 60° F. until waxy solids precipitate. A third method for producing clarified neem oil is to treat crude neem oil with a lipid-degrading enzyme under suitable temperature conditions until lipid degradation is substantially complete. In either case, solid material can be removed from the oil using known methods such as centrifugation or filtration.

Clarified neem oil, which is an orange-brown liquid at room temperature, has a very low phytotoxicity and causes little or no irritation on contact with plant surfaces. It exhibits the ability to kill not only insect larvae, but also insects in the egg and adult stage. Application at the egg stage causes large numbers of the eggs to shrivel, eliminating hatching. Where hatching occurs, many nymphs die upon emergence from the egg case. Treatment of plants also acts to repel adult insects, preventing eggs from being deposited. In addition, this neem oil fraction is a potent foliar and skin fungicide, which can be used to treat exemia and dermatitis.

In certain of the examples that follow, azadirachtin was provided to the compositions by adding a commercial concentrate containing a known percentage of azadirachtin. Alternatively, it is possible to use purified azadirachtin prepared according to methods known to the art. Clarified neem oil can also contain a low level of residual azadirachtin. For purposes of this application, this low level is insignificant and has not been included in the determination of azadirachtin concentration.

Also, while the accompanying examples demonstrate that the present invention permits PBO to be reduced or eliminated from pyrethrum-containing formulations, it is also true PBO is present in many commercial preparations of pyrethrum. Accordingly, while PBO is not necessary in the formulations of the present invention, as a practical matter it will often be present in the formulation. PBO is not detrimental to the formulations of the present invention, and, if present, can serve to further reduce the need for azadirachtin or clarified neem oil.

The formulations of this invention are effective to control such insect pests as Colorado potato beetle, diamondback moth, whitefly, mealy bug, aphids, hornworm, lace bug, fleas, mosquitos, and flies and the like. Furthermore, the compositions can be used to control non-insect pests on mammals such as lice, ticks, mites, scabies. The formulations may be used in any situation for which Pyrethrum alone is effective as a pest control agent.

In the compositions and formulations of the invention, the components may be mixed with conventional inert agronomically or physiology acceptable (i.e., plant and mammal compatible and/or insecticidally inert) diluents or extenders usable in conventional compositions or formulations as is well known in the art. If desired, adjuvants such as surfactants, stabilizers, antifoam agents and antidrift agents may also be added. Examples of compositions and formulations according to the invention include aqueous and other agronomically acceptable suspensions and dispersions, oily dispersions, pastes, dusting powders, wettable powders, emulsifiable concentrates, flowables, granules, baits, inert emulsions, aerosol compositions and fumigating candles.

The compositions and formulations are prepared in a known manner to one skilled in the art, for example by extruding the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as carboxymethylcellulose and natural and synthetic polymers in the form of powders, granules, or lattices, such as gum arabic, polyvinyl alcohol, polyvinyl cellulose, and polyvinyl acetate, can be used in the formulations to improve the adherence of this insecticide. Furthermore, a lubricant such as calcium stearate or magnesium stearate may be added to a wettable powder or to a mixture to be granulated.

One or more surfactants may typically be used in preparing the insecticide formulations. Non-ionic surfactants would generally be preferred. Examples include, but are not limited to, Triton B-1956, Tween-20, sodium dodecylsulfide and the like. For certain applications, anionic surfactants (such as Ivory liquid soap or the like) may be preferred. Where aqueous diluents or ingredients are used, an emulsifying surfactant should be used. Selection of surfactants, inert ingredients and diluents will depend on the application and are well known to those of ordinary skill in the art.

EXAMPLES

1. TEST PROCEDURES

The following procedures were followed throughout to test control of adult and nymphal whiteflies.

a. Adult Greenhouse Whitefly Bioassay. A healthy tomato leaf was selected. The leaf was then placed into a water-filled plastic jar that was secured with laboratory wax film (Parafilm). In each study, a leaf was sprayed, to run off, with an appropriate dilution of a test formulation or with a water control. Several dilutions of each formulation were tested to permit an $LD_{50}$ to be determined. The excess liquid was shaken off the leaf and the leaf was placed into a one gallon glass jar. A known number of adult greenhouse whiteflies were anesthetized and placed in the jar. The jar was then sealed with gauze. After approximately 1 hour, the number of whiteflies killed in the transfer process were counted. This number was subtracted from the number of dead flies at the end of the trial. The total number of dead whiteflies was determined after 24 hours. A whitefly was counted as dead if it was not moving or if it was moribund. The percent of whiteflies killed by each formulation was determined and then the data for all formulations were compared for efficacy.

b. Nymphal Greenhouse Whitefly Bioassay. Healthy tomato plants were placed in the USDA greenhouse whitefly colony for 24 to 48 hours, during which time eggs were deposited on the tomato plants by the adult flies. The plants were then removed from the colony greenhouse and all adult whiteflies were shaken from the plants. When the eggs hatched in approximately 10 days, leaves bearing large numbers of nymphs were tagged and treated with a test formulation. The number of living and dead nymphs were counted after adults emerged from the control plants treated with water only. Adults emerged from the control plants at about 10–14 days post treatment. The percent mortality was calculated for each formulation and then all of the formulations were compared for efficacy.

2. INITIAL BIOASSAY TRIAL RESULTS ON ADULT GREENHOUSE WHITEFLIES

Table 1 reports initial investigation by the applicants into the effectiveness of formulations containing Pyrethrum and azadirachtin at various concentrations. In addition, certain of the formulations contain Pipronyl butoxide (PBO) and/or clarified neem oil. The bioassays were performed as described in Example 1. Several dilutions of formulas were tested. The results of Table 1 demonstrate that pyrethrum at a low concentration (formulation 001) is comparably effective at controlling whiteflies as pyrethrum at a higher concentration (formulation 003), if neem oil is present in the low-pyrethrum formulation.

TABLE 1

| Formula | % AZAD | % Pyret | % Neem Oil | % PBO | Live | Dead | % Mortality |
|---|---|---|---|---|---|---|---|
| 0001 | 0.000625 | 0.002 | 0.02 | 0.1 | 44 | 269 | 85.94 |
| 0002 | 0.00625 | 0.0005 | 0.0485 | 0.25 | 86 | 227 | 72.52 |
| 0003 | 0.0017 | 0.087 | 0 | 0 | 7 | 98 | 93.33 |
|  | 0.00084 | 0.043 | 0 | 0 | 63 | 206 | 76.58 |
| 0004 | 0.0017 | 0.034 | 0 | 0.270 | 1 | 104 | 98.11 |
|  | 0.00084 | 0.017 | 0 | 0.270 | 10 | 250 | 96.15 |
| 0005 | 0.0017 | 0.058 | 0.145 | 0 | 4 | 18 | 81.82 |
|  | 0.00084 | 0.029 | 0.072 | 0 | 55 | 102 | 64.97 |
| 0006 | 0.0017 | 0.087 | 0 | 0.072 | 0 | 24 | 100.00 |
|  | 0.00084 | 0.043 | 0 | 0.036 | 8 | 196 | 96.08 |
| 0007 | 0.0007 | 0.058 | 0 | 0.145 | 1 | 35 | 97.22 |
|  | 0.00084 | 0.029 | 0 | 0.072 | 30 | 242 | 88.97 |

3. EVALUATION OF ADDITIONAL FORMULATIONS ON ADULT AND LARVAL GREENHOUSE WHITEFLIES

Formulations 1 and 4 from the previous example were selected as the bases for further analysis, using subformulations of formulas 1 and 4, to determine the role of each component and the preferred formulation for insect control.

The formulations and subformulations set forth in Table 2 were tested against adult and nymphal greenhouse whiteflies and the following results were obtained.

TABLE 2

| Formula | % AZAD | % Pyreth | % Neem Oil | % PBO | % Adult Mortality | % Nymphal Mortality |
|---|---|---|---|---|---|---|
| 1 | 0.000625 | 0.002 | 0.02 | 0.10 | 82.68% | 71.86% |
|  | 0.00031 | 0.0010 | 0.01 | 0.05 | 63.88% | 39.47% |
| 1A | 0.000625 | 0.002 | 0.02 | 0.02 | 79.67% | 31.56% |
|  | 0.0003 | 0.0010 | 0.01 | 0.01 | 84.97% | 27.08% |
| 1B | 0.0 | 0.002 | 0.02 | 0.02 | 76.82% | 28.40% |
|  | 0.0 | 0.0010 | 0.01 | 0.01 | 69.53% | 33.15% |
| 4 | 0.00163 | 0.0337 | 0 | 0.054 | 98.45% | 95.26% |
|  | 0.0008 | 0.0169 | 0 | 0.1349 | 95.45% | 55.68% |
| 4A | 0.00163 | 0.0337 | 0.1446 | 0 | 83.69% | 72.27% |
|  | 0.0008 | 0.0169 | 0.0723 | 0 | 88.84% | 55.57% |
| 4B | 0.0016 | 0.0554 | 0.1446 | 0 | 88.83% | 63.77% |
|  | 0.0008 | 0.0277 | 0.0723 | 0 | 94.32% | 41.16% |

4. COMPARISON OF FORMULATIONS TO COMMERCIAL PREPARATION CONTAINING PYRETHRUM AND PIPRONYL BUTOXIDE

A commercial preparation by Safer containing 0.011% Pyrethrum and 0.45 Pipronyl Butoxide, but lacking azadirachtin and clarified neem oil, was tested against three of the formulations prepared. The following mortality results were observed.

TABLE 3

| Treatment | Azadirachtin | Pyrethrum | PBO | Clar. Neem Oil | Adult Kill % |
|---|---|---|---|---|---|
| 0003 | .0002 | .011 | .0 | .0 | 13 |
| Safer | .0000 | .011 | .4 | .0 | 73 |
| 0004 | .0008 | .0169 | .1344 | .0 | 89 |
| 004A | .0008 | .0169 | .0 | .072 | 94 |

The above results demonstrate that azadirachtin at 0.0002% does not synergize with Pyrethrum to achieve mortality levels comparable to those of the commercial product. However, when the azadirachtin level is raised to 0.0008% and clarified neem oil is added to 0.075%, mortality is increased by at least 16 percentage points over that achieved by the commercial product.

5. MORTALITY RATES ACHIEVED USING FORMULATIONS HAVING VERY LOW LEVELS OF PYRETHRUM

Diluted formulations comprising Pyrethrum at 0.001% were tested for control of adult greenhouse whiteflies in the manner described above. These results show that addition of clarified neem oil at 0.01% provides acceptable 70% adult mortality. Notably, if 0.0003% azadirachtin is also added, mortality increases by 15%. When both azadirachtin and clarified neem oil was present, superior results were also obtained at low PBO levels.

TABLE 4

| Treatment | Azadirachtin | Pyrethrum | PBO | Clar. Neem Oil | Adult Kill % |
|---|---|---|---|---|---|
| 0001B | .0 | 0.001 | 0.01 | .01 | 70 |
| 0001 | .0003 | 0.001 | .05 | .01 | 64 |
| 0001A | .0003 | 0.001 | .01 | .01 | 85 |

An additional set of diluted formulations, each comprising Pyrethrum at 0.002%, were tested for biocontrol of adult greenhouse whiteflies. These data, shown in the table below demonstrate that at exceedingly low concentrations a synergistic effect of azadirachtin and clarified neem oil on Pyrethrum is not observed. However, acceptable control is observed at an azadirachtin level of 0.006% and a clarified neem oil concentration of 0.025%. It was also observed that there was no appreciable difference in insect control when the amount of Pipronyl butoxide was reduced from 0.1% to 0.02%, if the formulation included suitable amounts of azadirachtin and clarified neem oil.

TABLE 5

| | WT % IN SOLUTION | | | | |
|---|---|---|---|---|---|
| TREATMENT | AZADIRACHTIN | PYRETHRUM | PBO | CLAR. NEEM OIL | ADULT KILL % |
| 0002 | .00025 | .002 | .10 | .002 | 22 |
| 0001 | .0006 | .002 | .10 | .025 | 83 |
| 0001A | .0006 | .002 | .02 | .025 | 80 |

We claim:

1. A composition having pest control activity, the composition comprising synergistic effective amounts of:

pyrethrum; and azadirachtin at a weight ratio of between 0.002 and 1 part per part of pyrethrum.

2. A composition as claimed in claim 1 comprising pyrethrum in the range of 0.002% and 0.02% by weight.

3. A composition having pest control activity, the composition comprising synergistic effective amounts of:

pyrethrum; and clarified neem oil at a weight ratio of between 0.1 and 100 parts per part of pyrethrum.

4. A composition as claimed in claim 3 comprising pyrethrum in the range of 0.002% and 0.02% by weight.

5. A composition having pest control activity, the composition comprising synergistic effective amounts of:

pyrethrum;

azadirachtin at a weight ratio of between 0.002 and 1 part per part of pyrethrum; and clarified neem oil at a weight ratio of between 0.1 and 100 parts per part of pyrethrum.

6. A composition as claimed in claim 5 comprising pyrethrum in the range of 0.002% and 0.02% by weight.

* * * * *